United States Patent
Malenfant et al.

(10) Patent No.: US 6,239,125 B1
(45) Date of Patent: May 29, 2001

(54) AZETIDINONE DERIVATIVES FOR THE TREATMENT OF HCMV INFECTIONS

(75) Inventors: Eric Malenfant, Rosemère; Jeffrey O'Meara, Laval; Robert Déziel, Mont-Royal; William W. Ogilvie, Rosemère, all of (CA)

(73) Assignee: Boehringer Ingelheim (Canada) Ltd., Laval (CA)

( * ) Notice: Subject to any disclaimer, the term of this patent is extended or adjusted under 35 U.S.C. 154(b) by 0 days.

(21) Appl. No.: 09/167,142

(22) Filed: Oct. 6, 1998

Related U.S. Application Data

(60) Provisional application No. 60/061,550, filed on Oct. 7, 1997.

(51) Int. Cl.$^7$ .................. C07D 205/08; C07D 227/087; A61K 31/397; A61K 31/522; A61P 31/22
(52) U.S. Cl. ........................... 514/210.02; 540/360
(58) Field of Search ............................ 540/360; 514/210, 514/210.02

(56) References Cited

U.S. PATENT DOCUMENTS

| | | |
|---|---|---|
| 5,100,880 | 3/1992 | Durette et al. . |
| 5,104,862 | 4/1992 | Durette et al. . |
| 5,229,381 | 7/1993 | Doherty et al. . |

FOREIGN PATENT DOCUMENTS

| | | |
|---|---|---|
| 0199630 | 10/1986 | (EP) . |
| 0377549 | 10/1989 | (EP) . |
| 2266527 | 11/1993 | (GB) . |
| WO 95/02579 | 1/1995 | (WO) . |

OTHER PUBLICATIONS

Borthwick, Bioorganic & Med. Chem. Letters 8, 365, 1998.*

Hagmann et al., Bioog. Med. Chem. Lett, 1992, vol. 2, p. 681.

Hagmann et al., J. Med. Chem. 1993, vol. 36, p. 771.

Shah et al., Bioorg. Med. Chem. Lett. 1993, vol. 3, p. 2295.

Finke et al., J. Med. Chem. 1995, vol. 38, p. 2449.

Kabayashi et al., Chemical Abstracts, vol. 124, Abs. 29520, 1996 for Japanese Patent Application 07242624 published Sep. 19, 1995 (Nippon Tabacco).

Boeheme et al., Annual Reports in Medicinal Chemistry, 1995, vol. 30, p. 139.

* cited by examiner

Primary Examiner—Mark L. Berch
(74) Attorney, Agent, or Firm—Robert P. Raymond; Alan R. Stempel; Mary-Ellen M. Devlin

(57) ABSTRACT

A compound of formula 1:

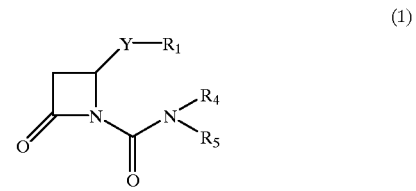

(1)

wherein Y is S or O;

$R_1$ is $C_{1-6}$ alkyl; ($C_{0-6}$ alkyl)aryl; ($C_{0-6}$ alkyl)Het; or $R_1$ is an amino acid analog or dipeptide analog of the formula:

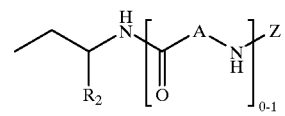

wherein $R_2$ is H, $C_{1-10}$ alkyl; or an amide or ester group;

A is $C_{6-10}$ aryl, Het or CH—$R_3$ wherein $R_3$ is $C_{1-6}$ alkyl or ($C_{0-4}$ alkyl)aryl; and Z is H, $C_{1-6}$ alkyl, or an acyl;

$R_4$ is hydrogen, lower alkyl, methoxy, ethoxy, or benzyloxy; and $R_5$ is alkyl, cycloalkyl, carboxyl group; an aryl;

Het or Het(lower alkyl); or $R_4$ and $R_5$ together with the nitrogen atom to which they are attached form a nitrogen containing ring optionally substituted with phenyl or C(O)OCH$_2$-phenyl, said phenyl ring optionally mono- or di-substituted with among others C(O)OR$_7$ wherein $R_7$ is lower alkyl or phenyl(lower alkyl); or a therapeutically acceptable acid addition salt thereof which compounds are useful in the treatment of HCMV infections.

16 Claims, No Drawings

AZETIDINONE DERIVATIVES FOR THE TREATMENT OF HCMV INFECTIONS

This application claims the benefit under 35 U.S.C. § 119 (e) of U.S. Provisional Application No. 60/061,550 filed Oct. 7. 1997.

FIELD OF THE INVENTION

This invention relates to azetidinone derivatives having activity against herpes infections. More specifically, the invention relates to azetidin-2-one derivatives exhibiting antiherpes activity, to pharmaceutical compositions comprising the derivatives, and methods of using the derivatives to inhibit the replication of herpes virus and to treat herpes infections.

BACKGROUND OF THE INVENTION

Herpes viruses inflict a wide range of diseases against humans and animals. For instance, herpes simplex viruses, types 1 and 2 (HSV-1 and HSV-2), are responsible for cold sores and genital lesions, respectively; varicella zoster virus (VZV) causes chicken pox and shingles; and the human cytomegalovirus (HCMV) is a leading cause of opportunistic infections in immunosuppressed individuals.

Over the past two decades, a class of compounds known as the purine and pyrimidine nucleoside analogs has received the most attention by investigators in the search for new therapeutic agents for treatment of herpes virus infections. As a result, several nucleoside analogs have been developed as antiviral agents. The most successful to date is acyclovir which is the agent of choice for treating genital HSV infections. Another nucleoside analog, ganciclovir, has been used with some success in treating HCMV infections.

Nevertheless, in spite of some significant advances, the need for effective, safe therapeutic agents for treating herpes viral infections continues to exist. For a review of current therapeutic agents in this area, see R. E. Boeheme et al., Annual Reports in Medicinal Chemistry, 1995, 30, 139.

Azetidin-2-one derivatives have been reported in the literature as having variety of biological activities; mainly antibacterial, anti-inflammatory, anti-degenerative, etc. However, azetidin-2-one derivatives have not been reported to be antiviral agents against herpes viruses.

The following references disclose azetidin-2-ones having biological activity:

S. K. Shah et al., European patent application 0,199,630, Oct. 29, 1986,

S. K. Shah et al., European patent application 0,377,549, Oct. 18, 1989,

P. L. Durette and M. Maccoss, U.S. Pat. No. 5,100,880, Mar. 31, 1992,

P. L. Durette and M. Maccoss, U.S. Pat. No. 5,104,862, Apr. 14, 1992,

W. K. Hagmann et al., *Bioorg. Med. Chem. Lett.* 1992, 2, 681,

W. K. Hagmann et al., *J. Med. Chem.* 1993, 36, 771,

J. B. Doherty et al., U.S. Pat. No. 5,229,381, issued Jul. 20, 1993,

S. K. Shah et al., *Bioorg. Med. Chem. Lett.* 1993, 3, 2295,

G. Crawley, PCT patent WO 95/02579, published Jan. 26, 1995,

P. E. Finke et al., *J. Med.Chem.* 1995, 38, 2449, and K. Kobayashi et al., Japanese patent application 07242624, published Sep. 19, 1995; *Chem. Abstr.* 1996, 124, 29520.

SUMMARY OF THE INVENTION

The present application discloses a group of azetidin-2-one derivatives particularly active against cytomegalovirus. This activity coupled with a wide margin of safety, renders these derivatives desirable agents for combating herpes infections.

The present azetidin-2-one derivatives are distinguished from the prior art compounds in that they possess different chemical structures and biological activities.

The azetidin-2-one derivatives are represented by formula 1:

$$(1)$$

wherein Y is S or O;

$R_1$ is $C_{1-6}$ alkyl optionally substituted with NHC(O)—$R_8$ or C(O)—$R_8$ wherein $R_8$ is a $C_{1-6}$ alkyl, O—$C_{1-6}$ alkyl, NH—$C_{1-6}$ alkyl, ($C_{0-4}$ alkyl)aryl or ($C_{0-4}$ alkyl)Het, wherein Het represents a five or six-membered, monovalent heterocyclic ring containing a heteroatom selected from the group consisting of N, O, or S;

($C_{0-6}$ alkyl)aryl, wherein said aromatic ring is optionally substituted with halo, $C_{1-6}$ alkyl, O—$C_{1-6}$ alkyl or NH-$R_9$ wherein $R_9$ is:

$C_{1-6}$ alkyl, $C_{6-10}$ aryl, Het, or an acyl of formula C(O)-$R_{10}$ wherein $R_{10}$ is a $C_{1-6}$ alkyl, O—$C_{1-6}$ alkyl, NH—$C_{1-6}$ alkyl, ($C_{0-4}$ alkyl)aryl or ($C_{0-4}$ alkyl)Het;

($C_{0-6}$ alkyl)Het the carbon atoms of said Het being optionally substituted with halo, $C_{1-6}$ alkyl, O-$R_9$ or NH-$R_9$ wherein $R_9$ is as defined above;

or the nitrogen atom of said Het being optionally substituted with $R_9$ wherein $R_9$ is as defined above; or $R_1$ is an amino acid analog or dipeptide analog of the formula:

wherein $R_2$ is H, $C_{1-10}$ alkyl optionally monosubstituted with ($C_{1-6}$ alkyl)thio, ($C_{1-6}$ alkyl)sulfonyl or $C_{6-10}$ aryl, or an amide or ester group mono- or di-substituted with $C_{1-6}$ alkyl;

A is $C_{6-10}$ aryl, Het or CH—$R_3$ wherein $R_3$ is $C_{1-6}$ alkyl or ($C_{0-4}$ alkyl)aryl; and Z is H, $C_{1-6}$ alkyl, or an acyl of formula C(O)-$R_8$ wherein $R_8$ is as defined above;

$R_4$ is hydrogen, lower alkyl, methoxy, ethoxy, or benzyloxy; and $R_5$ is lower alkyl, lower cycloalkyl, $(CH_2)_m$—C(O)O$R_6$ wherein m is the integer 1 or 2 and $R_6$ is lower alkyl or phenyl(lower alkyl);

phenyl, phenyl monosubstituted, disubstituted or trisubstituted with a substituent selected independently from the group consisting of:

lower alkyl, lower alkoxy, lower alkylthio, halo, hydroxy and amino; phenyl(lower alkyl), phenyl(lower alkyl) monosubstituted or disubstituted on the phenyl portion thereof with a substituent selected independently from the group consisting of lower alkyl, lower alkoxy, lower alkylthio, halo, hydroxy, nitro, amino, lower alkylamino, di(lower alkyl)amino, lower acylamino, di(lower alkyl)aminocarbonyl, cyano, trifluoromethyl, (trifluoromethyl)thio, (trifluoromethyl)sulfinyl, (trifluoromethyl)sulfonyl and C(O)OR$_7$ wherein R$_7$ is lower alkyl or phenyl(lower alkyl);

Het or Het(lower alkyl) wherein Het represents an unsubstituted, monosubstituted or disubstituted five or six membered, monovalent heterocyclic ring containing one or two heteroatoms selected from the group consisting of N, O or S, wherein each substituent is selected independently from the group consisting of lower alkyl, lower alkoxy, halo and hydroxy;

5-(benzo[1,3]dioxolyl) methyl, (1(R)-1-naphthalenyl) ethyl, 2-benzothiazolyl or 2-thiazolo[4,5-b]pyridinyl; or R$_4$ and R$_5$ together with the nitrogen atom to which they are attached form a piperidino, morpholino, thiomorpholino, piperazino, N-methylpiperazino, 1-(3,4-dihydro-1H-isoquinolinyl) or 2-(3,4-dihydro-1H-isoquinolinyl) or a pyrrolidino ring optionally substituted with phenyl or C(O)OCH$_2$-phenyl, said phenyl ring optionally mono- or di-substituted with a substituent selected independently from the group consisting of lower alkyl, lower alkoxy, lower alkylthio, halo, hydroxy, nitro, amino, lower alkylamino, di(lower alkyl)amino, lower acylamino, di(lower alkyl) aminocarbonyl, cyano, trifluoromethyl, (trifluoromethyl)thio, (trifluoromethyl)sulfinyl, (trifluoromethyl)sulfonyl and C(O)OR$_7$ wherein R$_7$ is lower alkyl or phenyl(lower alkyl); or a therapeutically acceptable acid addition salt thereof.

Preferred compounds of the invention include compounds of formula (1) wherein Y is S or O; R$_1$ is C$_{1-6}$ alkyl optionally substituted with C(O)—R$_8$ or NHC(O)—R$_8$ wherein R$_8$ is a C$_{1-6}$ alkyl, NH—C$_{1-6}$ alkyl or phenyl;

(C$_{0-4}$ alkyl)phenyl wherein said phenyl ring is optionally substituted with halo, C$_{1-6}$ alkyl, or NH-R$_9$, wherein R$_9$ is:
  C$_{1-4}$ alkyl, phenyl or an acyl of formula C(O)—R$_{10}$ wherein R$_{10}$ is a C$_{1-6}$ alkyl, NH—C$_{1-6}$ alkyl or phenyl;
(C$_{0-3}$ alkyl)Het wherein said carbon atoms of said Het is optionally substituted with halo, C$_{1-6}$ alkyl or NH-R$_9$;
or said nitrogen atom of said Het is substituted with R$_9$, wherein R$_9$ is:
C$_{1-4}$ alkyl, phenyl or an acyl of formula C(O)—R$_{10}$ wherein R$_{10}$ is a C$_{1-6}$ alkyl, NH—C$_{1-6}$ alkyl or phenyl; or R$_1$ is an amino acid analog or dipeptide analog of formula:

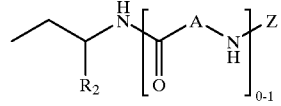

wherein R$_2$ is H, the side chain of asparagine optionally N-alkylated, or C$_{1-6}$ alkyl optionally monosubstituted with (C$_{1-6}$ alkyl)sulfonyl or phenyl;

A is phenyl or CH—R$_3$ wherein R$_3$ is C$_{1-6}$ alkyl or (C$_{0-4}$ alkyl)phenyl; and Z is C(O)—R$_8$ wherein R$_8$ is C$_{1-6}$ alkyl, C$_{1-6}$ alkoxy or phenyl;

R$_4$ is hydrogen or C$_{1-3}$ alkyl; and

R$_5$ is phenyl optionally substituted with a substituent selected independently from the group consisting of lower alkyl, lower alkoxy; phenyl(lower alkyl) optionally mono- or di-substituted on the phenyl portion thereof with a substituent selected independently from the group consisting of lower alkyl, lower alkoxy, nitro, halo, cyano, trifluoromethyl, and C(O)OR$_7$ wherein R$_7$ is lower alkyl or (lower alkyl)phenyl;

Het(lower alkyl) wherein Het represents a five or six-membered, monovalent heterocyclic ring containing a heteroatom selected from the group consisting of N, O, or S, said ring being optionally substituted with lower alkyl or lower alkoxy;

or R$_4$ and R$_5$ together with the nitrogen atom to which they are attached form a pyrrolidino optionally substituted with C(O)O-benzyl or phenyl said phenyl ring optionally mono- or di-substituted with halo, nitro, cyano or trifluoromethyl; or a therapeutically acceptable acid addition salt thereof.

More preferred compounds of the invention include compounds of formula 1 wherein Y is S or O; R$_1$ is C$_{1-3}$ alkyl optionally substituted with C(O)OMe or NH—C(O)—Ph;

phenyl, benzyl or phenylethyl wherein said phenyl ring is optionally substituted with chloro or methoxy;

Het, Het-methyl or Het-ethyl, wherein Het is 2-, 3-, or 4-pyridinyl optionally substituted on the nitrogen by methyl or C(O)—R$_{10}$ wherein R$_{10}$ is CH$_2$-t-Bu or phenyl; or R$_1$ is an amino acid analog or dipeptide analog of formula:

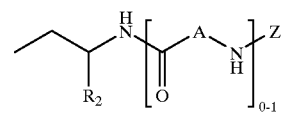

wherein R$_2$ is H, CH$_2$—C(O)N(Me)$_2$, CH$_2$—CH(Me)$_2$ or methyl optionally monosubstituted with methylsulfonyl;

A is phenyl or CH-t-Bu; and

Z is C(O)—R$_8$ wherein R$_8$ is CH$_2$-t-Bu or 0-t-Bu;

R$_4$ is hydrogen or lower alkyl; and

R$_5$ is phenyl optionally substituted with a substituent selected independently from the group consisting of lower alkyl, lower alkoxy; (C$_{1-2}$ alkyl)phenyl optionally mono- or di-substituted on the phenyl portion thereof with a substituent selected independently from the group consisting of lower alkyl, lower alkoxy, nitro, halo, cyano, trifluoromethyl, and C(O)OR$_7$ wherein R$_7$ is lower alkyl or (lower alkyl)phenyl; or a therapeutically acceptable acid addition salt thereof.

A most preferred group of compounds is represented by formula 1':

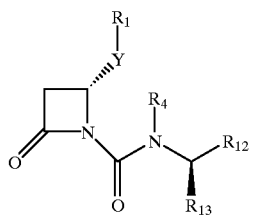

(1')

wherein Y is O or S;

$R_1$ is phenyl, 4-chloro-phenyl, benzyl, phenylethyl, 2-pyridinylmethyl, 3-pyridinylmethyl, 4-pyridinylmethyl, $CH_2$—(S)CH($CH_2CH_2SO_2Me$)—NH—Tbg—Boc, $CH_2$—(S)CH($CH_2CHMe_2$)—NH—Tbg—C(O)$CH_2$-t-Bu;

$R_4$ is H or Me;

$R_{12}$ is phenyl, benzyloxyethyl or Het; and $R_{13}$ is hydrogen, methyl, ethyl, propyl or hydroxymethyl.

Included within the scope of this invention is a pharmaceutical composition for treating cytomegalovirus infections in a human comprising a compound of formula 1, or a therapeutically acceptable salt thereof, and a pharmaceutically acceptable carrier.

The scope of the invention also includes a method for treating cytomegalovirus infections in a human comprising administering thereto an effective amount of the compound of formula 1, or a therapeutically acceptable salt thereof.

Also included within the scope is a method for protecting human cells against cytomegalovirus pathogenesis comprising treating said infected cells with an anti-cytomegalovirus effective amount of a compound of formula 1, or a therapeutically acceptable salt thereof.

Compounds of formula 1 according to the present invention may also be used in co-therapies with other conventional anti-herpes compounds, such as but not limited to ganciclovir, foscarnet, acyclovir, valacyclovir, famciclovir, cidofovir, penciclovir, and lobucavir.

Compounds of formula 1 according to the present invention may also be used in co-therapies with anti-retroviral compounds such as reverse transcriptase inhibitors (i.e. AZT, 3TC) or protease inhibitors.

Process for preparing the compounds of formula 1 are described hereinafter.

DETAILED DESCRIPTION OF THE INVENTION

General

As used herein, the following definitions apply unless otherwise noted:

With reference to the instances where (R) or (S) is used to designate the configuration of a radical, e.g. $R_5$ of the compound of formula I, the designation is done in the context of the compound and not in the context of the radical alone.

The term "residue" with reference to an amino acid or amino acid derivative means a radical derived from the corresponding α-amino acid by eliminating the hydroxyl of the carboxy group and one hydrogen of the α-amino group. For instance, the terms Gln, Ala, Gly, Ile, Arg, Asp, Phe, Ser, Leu, Cys, Asn, Sar and Tyr represent the "residues" of L-glutamine, L-alanine, glycine, L-isoleucine, L-arginine, L-aspartic acid, L-phenylalanine, L-serine, L-leucine, L-cysteine, L-asparagine, sarcosine and L-tyrosine, respectively.

The term "side chain" with reference to an amino acid or amino acid derivative means a residue attached to the α-carbon atom of the α-amino acid. For example, the R-group side chain for glycine is hydrogen, for alanine it is methyl, for valine it is isopropyl. For the specific R-groups or side chains of the α-amino acids reference is made to A. L. Lehninger's text on Biochemistry (see chapter 4).

The term "halo" as used herein means a halo radical selected from bromo, chloro, fluoro or iodo.

The term "lower alkyl" (or $C_{1-6}$ alkyl) as used herein, either alone or in combination with another radical, means straight or branched-chain alkyl radicals containing up to six carbon atoms and includes methyl, ethyl, propyl, butyl, hexyl, 1-methylethyl, 1-methylpropyl, 2-methylpropyl and 1,1-dimethylethyl. The term "$C_{0-6}$ alkyl" preceding a radical means that this radical can optionally be linked through a $C_{1-6}$ alkyl radical or the alkyl may be absent ($C_0$).

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tert-butoxy.

The term "lower cycloalkyl" as used herein, either alone or in combination with another radical, means saturated cyclic hydrocarbon radicals containing from three to seven carbon atoms and includes cyclopropyl, cyclobutyl, cyclopentyl, cyclohexyl and cycloheptyl.

The term "amino" as used herein means an amino radical of formula —$NH_2$. The term "lower alkylamino" as used herein means alkylamino radicals containing one to six carbon atoms and includes methylamino, propylamino, (1-methylethyl)amino and (2-methylbutyl)amino. The term "di(lower alkyl)amino" means an amino radical having two lower alkyl substituents each of which contains one to six carbon atoms and includes dimethylamino, diethylamino, ethylmethylamino and the like.

The term "Het" as used herein means a monovalent radical derived by removal of a hydrogen from a five- or six-membered saturated or unsaturated heterocycle containing from one to four heteroatoms selected from nitrogen, oxygen and sulfur. Optionally, the heterocycle may bear one or two substituents; for example, N-oxido, lower alkyl, ($C_{1-3}$)alkyl-phenyl, lower alkoxy, halo, amino or lower alkylamino. Again optionally, the five- or six-membered heterocycle can be fused to a phenyl. Examples of suitable heterocycles and optionally substituted heterocycles include pyrrolidine, tetrahydrofuran, thiazolidine, pyrrole, 1H-imidazole, 1-methyl-1H-imidazole, pyrazole, furan, thiophene, oxazole, isoxazole, thiazole, 2-methylthiazole, 2-aminothiazole, 2-(methylamino)-thiazole, piperidine, 1-methylpiperidine, 1-methylpiperazine, 1,4-dioxane, morpholine, pyridine, pyridine N-oxide, pyrimidine, 2,4-dihydroxypyrimidine, 2,4-dimethylpyrimidine, 2,6-dimethylpyridine, 1-methyl-1H-tetrazole, 2-methyl-2H-tetrazole, benzothiazole, benzoxazole and thiazolo[4,5-b]-pyridine.

The term "pharmaceutically acceptable carrier" as used herein means a non-toxic, generally inert vehicle for the active ingredient which does not adversely affect the ingredient.

The term "effective amount" means a predetermined antiviral amount of the antiviral agent, i.e. an amount of the agent sufficient to be effective against the virus in vivo.

The azetidin-2-one derivatives of formula I can be obtained in the form of therapeutically acceptable acid addition salts. In the instance where a particular derivative has a residue which functions as a base, examples of such salts are those with organic acids, e.g. acetic, lactic, succinic, benzoic, salicylic, methanesulfonic or p-toluenesulfonic acid, as well as polymeric acids such as tannic acid or carboxymethyl cellulose, and salts with inorganic acids such as hydrohalic acids, e.g. hydrochloric acid, or sulfuric acid, or phosphoric acid.

Process

Compounds of formula 1 can be synthesized from commercially available, suitably protected amino acids, as exemplified hereinafter. (For general synthetic procedures see: *The Organic Chemistry of beta-Lactams*, Gunda I. Georg, Ed.; VCH Publishers Inc., New York, N.Y., USA, 1992, pp 1 to 48 and 257 to 293.)

A) The compound of formula 1 wherein Y, $R_1$, $R_2$, $R_3$ and $R_5$ are as defined hereinabove and $R_4$ is hydrogen can be prepared by the following processes:

Scheme A

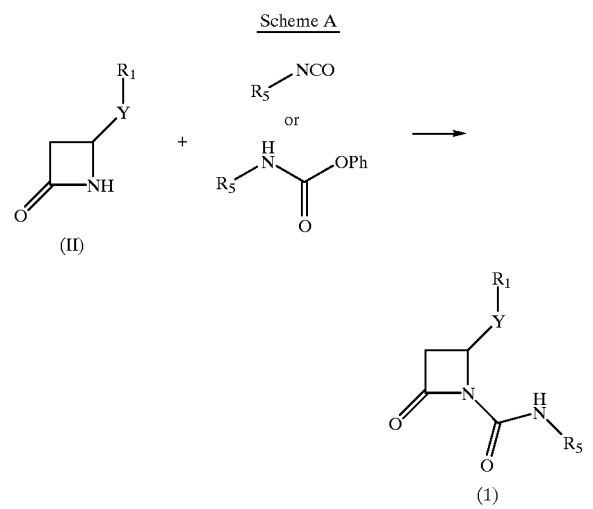

(a) reacting a key intermediate of formula II with an isocyanate of formula RSNCO wherein $R_5$ is as defined herein in the presence of a proton acceptor, or b) reacting a key intermediate of formula II with a phenoxycarbamate of formula $R_5NHC(O)O$—Ph in the presence of a proton acceptor, to obtain the corresponding compound of formula 1 wherein $R_4$ is hydrogen.

B) The compound of formula 1 wherein Y, $R_1$, $R_2$, $R_3$ and $R_5$ are as defined hereinabove and $R_4$ is not hydrogen can be prepared by the following process:

Scheme B

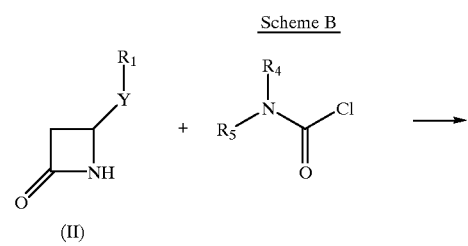

-continued

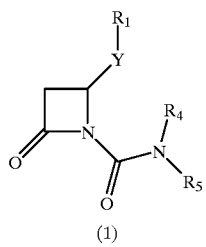

reacting the key intermediate of formula II with a carbamoyl chloride derivative of formula $R_4R_5NC(O)Cl$ wherein $R_4$ is lower alkyl and $R_5$ is as defined hereinabove, or $R_4$ and $R_5$ together with the nitrogen atom to which they are attached form a pyrrolidino, piperidino or morpholino in the presence of a proton acceptor to obtain the corresponding compound of formula I wherein $R_1$ and $R_5$ are as defined hereinabove, and $R_4$ is lower alkyl, or $R_4$ and $R_5$ together with the nitrogen atom to which they are attached are as defined herein.

The aforementioned key intermediate of formula II wherein Y is oxygen, can be prepared by a process illustrated by Scheme C as follows:

Scheme C

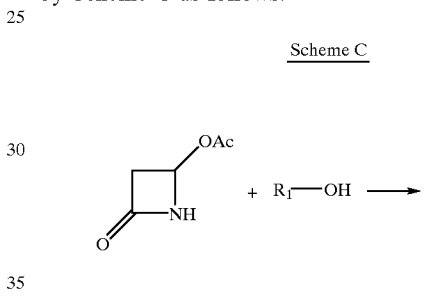

As exemplified in Step A, example 4.

The aforementioned key intermediate of formula II wherein Y is sulfur, can be prepared by a process illustrated by Scheme D as follows:

Scheme D

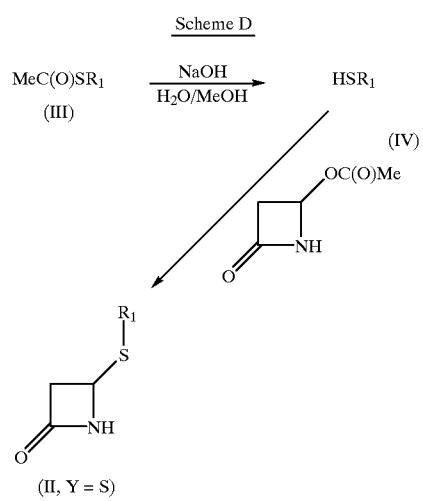

As exemplified by step C of example 1.

Antiherpes Activity

The antiherpes activity of the aforementioned azetidinone derivatives of formula 1 (HCMV protease inhibitors) can be demonstrated by biochemical, microbiological and biological procedures.

A biochemical procedure for demonstrating anti-cytomegalovirus activity for the azetidinone derivatives of formula 1 is described in the examples hereinafter. This particular assay determines the ability of a test compound to inhibit the activity ($IC_{50}$) of HCMV protease. More specifically, in the assay described herein, the inhibitory activity of the test compound is evaluated on the basis of its ability to interfere with the HCMV No protease cleavage of a fluorogenic peptide substrate which in turn is based on the maturation cleavage site of the enzyme.

Methods for demonstrating the inhibiting effect of the azetidinone derivatives of formula 1 on CMV replication involving cell culture techniques ($EC_{50}$) are described in the examples herein.

When the HCMV protease inhibitor is employed as an antiviral agent, it is administered orally, or systemically to humans in a vehicle comprising one or more pharmaceutically acceptable carriers, the proportion of which is determined by the solubility and chemical nature of the compound, chosen route of administration and standard biological practice. For oral administration, the compound or a therapeutically acceptable salt thereof can be formulated in unit dosage forms such as capsules or tablets each containing a predetermined amount of the active ingredient, ranging from about 50 to 500 mg, in a pharmaceutically acceptable carrier.

For parenteral administration, the HCMV protease inhibitor is administered by either intravenous, subcutaneous or intramuscular injection, in compositions with pharmaceutically acceptable vehicles or carriers. For administration by injection, it is preferred to use the compounds in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in standard pharmaceutical texts, e.g. in "Remington's The Science and Practice of Pharmacy", 19th ed., Mack Publishing Company, Easton, Pa., 1995, or in "Pharmaceutical Dosage Forms and Drug Delivery Systems", 6th ed., H. C. Ansel et al., Eds., Williams & Wilkins, Baltimore, Md., 1995.

The dosage of the HCMV protease inhibitor will vary with the form of administration and the particular active agent chosen. Furthermore, it will vary with the particular host under treatment. Generally, treatment is initiated with small increments until the optimum effect under the circumstance is reached. In general, the inhibitor compound is most desirably administered at a concentration level that will generally afford anti-virally effective results without causing any harmful or deleterious side effects.

For oral administration, the HCMV protease inhibitor is administered in the range of 20 to 200 mg per kilogram of body weight per day, with a preferred range of 25 to 100 mg per kilogram.

For ocular administration, the HCMV protease inhibitor is administered either topically or intraocularly (injection or implant) in a suitable preparation. For example, an implant containing the compound in a suitable formulation can be surgically implanted in the posterior segment of the eye through a small incision.

With reference to systemic administration, the HCMV protease inhibitor is administered at a dosage of 10 mg to 150 mg per kilogram of body weight per day, although the aforementioned variations will occur. However, a dosage level that is in the range of from about 10 mg to 100 mg per kilogram of body weight per day is most desirably employed in order to achieve effective results.

EXAMPLES

The following examples further illustrate this invention. All reactions were performed in a nitrogen or argon atmosphere. Temperatures are given in degrees Celsius. Solution percentages or ratios express a volume to volume relationship, unless stated otherwise. Nuclear magnetic resonance spectra were recorded on a Bruker 400 MHz spectrometer; the chemical shifts (δ) are reported in parts per million. Abbreviations or symbols used herein include DEAD: diethyl azodicarboxylate; DIEA: diisopropylethylamine; DMAP: 4-(dimethylamino)pyridine; DMF: dimethylformamide; Et: ethyl; EtOAc: ethyl acetate; $Et_2O$: diethyl ether; Me: methyl; MeOH: methanol; MeCN: acetonitrile; Ph: phenyl; TBTU: 2-(1H-benzotriazol-1-yl)-N,N, N',N'-tetramethyluronium tetrafluoroborate; THF: tetrahydrofuran; MS (FAB) or FAB/MS: fast atom bombardment mass spectrometry; HRMS: high resolution mass spectrometry; PFU: plaque forming units.

Example 1

Preparation of (2-oxo-4(S)-(pyridin-2-yl-methylthio)azetidine-1-carboxylic acid (1(R)-phenylpropyl) amide hydrochloride (7) (Table 1, entry #114)

Step A 2-picolyl thioacetate (2)

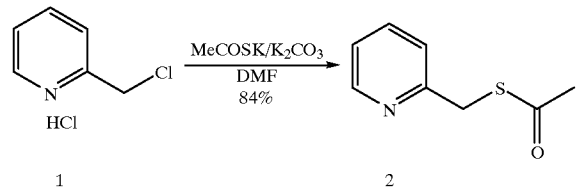

Potassium thioacetate (8.4 g, 73 mmol), 2-picolyl chloride hydrochloride 1 (6.0 g, 37 mmol) and potassium carbonate (5.0 g, 37 mmol) were stirred in DMF (35 mL) at room temperature (20–22°) for 18 h. The reaction mixture was poured into water (200 mL). The resultant mixture was extracted with $Et_2O$ (2×50 mL). The combined organic phases were washed with water and brine, dried ($MgSO_4$), filtered and concentrated to give 2-picolyl thioacetate as a pale brown liquid (5.65 g). The product was used without purification.

$^1$H NMR (400 MHz, $CDCl_3$) δ 8.51 (d, 1H), 7.62 (t, 1H), 7.32 (d, 1H), 7.15 (d, 1H), 4.25 (s, 2H), 2.37 (s, 3H).

Step B 1(R)-phenylpropyl isocyanate (4)

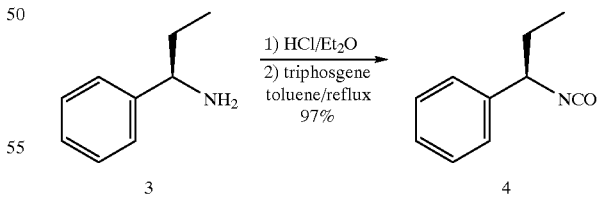

To a solution of (1(R)-phenylpropyl)amine 3 (14.3 g, 106 mmol) in $Et_2O$ (102 mL) was added a 1.0 M solution of HCl /$Et_2O$ (212 mL, 212 mmol), stirred for 30 min and then the crude solution was evaporated to dryness on a rotary evaporator. The resulting white hydrochloride salt was suspended in toluene (200 mL) and triphosgene was added (11.7 g, 39.3 mmol) and the resulting suspension was stirred under reflux for 3 h and then at room temperature for 18 h. The reaction mixture was concentrated and the final volume adjusted to 200 mL in toluene to give a final concentration of 0.53M. The resulting isocyanate solution of 4 was used as such.

An aliquot (170 μL) was concentrated to give 1(R)-phenylpropyl isocyanate as a colorless oil.

$^1$H NMR (400 MHz, CDCl$_3$) δ 7.36–7.22 (m, 5H), 4.50 (t, J=6.7 Hz, 1H), 1.82 (q, J=7.3 Hz, 2H), 0.94 (t, J=7.3 Hz, 2H)

Step C 4-{(2-pyridinylmethyl)thio}azetidin-2-one (6)

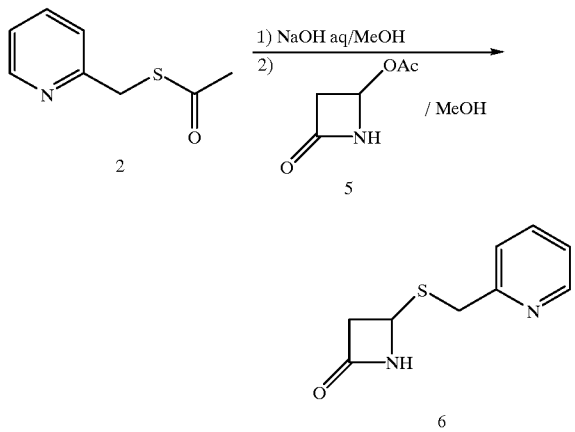

To a solution of 2-picolyl thioacetate 2 (from step A) (673 mg, 4.00 mmol) in MeOH (8 mL) was added a 5M solution of sodium hydroxide in water (890 μL, 4.40 mmol). After 15 min of stirring at room temperature, a solution of 4-acetoxyazetidin-2-one 5 (520 mg, 4.00 mmol) in MeOH (1.5 mL) was added. The reaction mixture was stirred for 2 h at room temperature, then concentrated under pressure. The residue was poured in water (30 mL) and extracted with EtOAc (3×15 mL), dried (MgSO$_4$), filtered and concentrated. The residue was purified by flash chromatography (SiO$_2$, EtOAc) to yield 4-{(2-pyridinylmethyl)-thio}azetidin-2-one 6 (750 mg, 96% yield) as a yellow oil.

$^1$H NMR (400 MHz, CDCl$_{13}$) δ 8.50 (d, 1H), 7.68 (t, 1H), 7.30 (d, 1H), 7.20 (t, 1H), 6.42 (br s, 1H), 4.88 (dd, 1H), 3.91 (s, 3H), 3.35 (dd, 1H), 2.85 (dd, 1H).

Step D 4(S)-{(2-pyridinylmethyl)thio}azetidin-2-one-1-carboxylic acid (1(R)-phenylpropyl)amide hydrochloride (7)

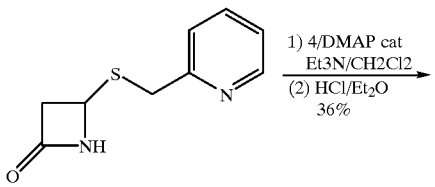

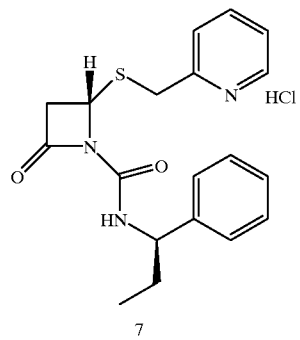

To a solution of the azetidinone 6 from step C (188 mg, 0.970 mmol), Et$_3$N (150 μL, 1.07 mmol), DMAP (10 mg) in CH$_2$Cl$_2$ (5 mL) was added a solution of 1(R)-phenylpropyl isocyanate 4 (172 mg, 1.07 mmnol) in CH$_2$Cl$_2$ (2 mL). The reaction mixture was stirred for 22 h. A second portion Of Et$_3$N (150 μL, 1.07 mmol), DMAP (10 mg) and 4 (172 mg, 1.07 mmol) in CH$_2$Cl$_2$ (2 mL) were added and the mixture was stirred for another 22 h. The mixture was concentrated under reduced pressure and the residue was purified by flash chromatography (SiO$_2$, 40% EtOAc-hexane) to afford the 4S isomer 7 (less polar isomer). Treatment with HCl in Et$_2$O (2 mL, 1M) gave 7 (74 mg, 19% yield) as a white solid. The starting material was recovered (90 mg, 48%).

$^1$H NMR (400 MHz, DMSO-D$_6$) δ 8.67 (d, J=4.8 Hz, 1H), 8.13 (t, J=7.0 Hz, 1H), 7.72 (d, J=8.0 Hz, 1H), 7.60 (t, J=7.7 Hz, 1H), 7.36–7.23 (m, 5H), 7.14 (d, J=8.3 Hz, 1H), 5.28–5.26 (m, 1H), 4.65 (q, J=7.3 Hz, 1H), 4.48 (d, J=14.3 Hz, 1H), 4.26 (d, J=14.3 Hz, 1H), 3.52 (dd, J=6.0, 16.2 Hz, 1H), 3.02 (dd, J=3.0, 16.2 Hz, 1H), 1.87–1.71 (m, 2H), 0.83 (t, J=7.0 Hz, 3H); IR (KBr) v 1768, 1689 cm$^{-1}$; FAB MS m/z 356 (MH$^+$); HRMS calcd for C$_{19}$H$_{22}$N$_3$O$_2$S$_1$: 356.1433 (MH$^+$); found: 356.1421

Example 2

Preparation of 4(S)-{{2(S)-{(N-tert-butyloxycarbonyl-L-tert-butylglycyl)amino}-4-methylpentyl]thio} azetidin-2-one-1-carboxylic acid benzylamide 13 (Table 1, entry 101)

Step A N-tert-butyloxycarbonyl-L-tert-butylglycyl-L-leucinol (10)

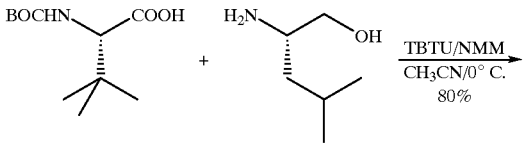

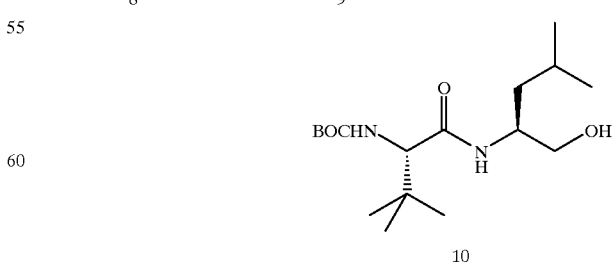

To a suspension of N-tert-butyloxycarbonyl-L-tert-butylglycine 8 (2.43 g, 10.5 mmol), L-leucinol 9 (1.23 g, 10.5 mmol) and TBTU (3.44 g, 11.5 mmol) in acetonitrile (30 mL) at 0° (ice bath) was added N-methyl morpholine (1.3 mL, 11.5 mmol). The resulting mixture was stirred 19 h (allowing the ice bath to warm to room temperature) and the white solid was collected on a filter (486 mg, 14% yield). The mother liquors were purified by flash chromatography (SiO$_2$, 25–35% EtOAc-hexane) affording N-tert-butyloxycarbonyl-L-tert-butylglycyl-L-leucinol 10 (2.79 g, 80% yield) as a white solid (including the filtered solid).

$^1$H NMR (400 MHz, CDCl$_3$) δ 5.82 (d, 1H), 5.19 (d, 1H), 4.09–4.00 (m, 1H), 3.76 (d, 1H), 3.69 (dd, 1H), 3.54 (dd, 1H), 1.69–1.59 (m, 1H), 1.44 (s, 9H), 1.43–1.28 (m, 2H), 1.02 (s, 9H), 0.93 (d, 3H), 0.91 (d, 3H).

Step B (N-tert-butyloxycarbonyl-L-tert-butylglycyl-S-acetyl-L-leucinethiol (11)

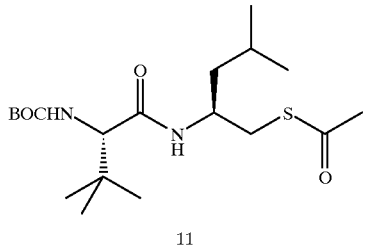

To a solution triphenylphosphine (373 mg, 1.42 mmol) and diethyl azodicarboxylate (225 µL, 1.42 mmol) in THF (6 mL) at 0° was added a solution of N-tert-butyloxy carbonyl-L-tert-butylglycyl-L-leucinol 10 (313 mg, 0.950 mmol) and thioacetic acid (100 µL, 1.42 mmol) in THF (4 mL). The mixture was stirred at 0° for 2 h and the solvent was removed under vacuum. The residue was purified by flash chromatography (SiO$_2$, 10–30% EtOAc-hexane) to give the corresponding title compound 11 in 63% yield (232 mg).

$^1$H NMR (400 MHz, CDCl$_3$) δ5.60 (d, 1H), 5.16 (d, 1H), 4.21–4.11 (m, 1H), 3.69 (d, 1H), 3.10–2.99 (m, 2H), 2.35 (s, 3H), 1.66–1.58 (m, 1H), 1.44 (s, 9H), 1.43–1.28 (m, 2H), 0.99 (s, 9H), 0.92 (d, 3H), 0.90 (d, 3H).

Step C 4-{{2(S)-{(N-tert-butyloxycarbonyl-L-tert-butylglycyl)amino}-4-methylpentyl}thio}azetidin-2-one (12)

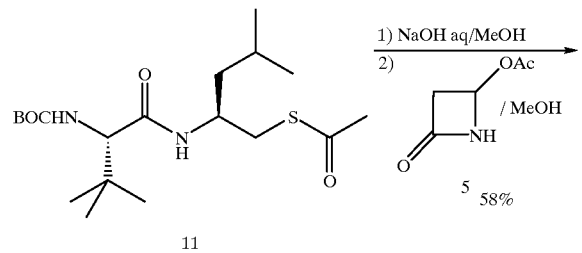

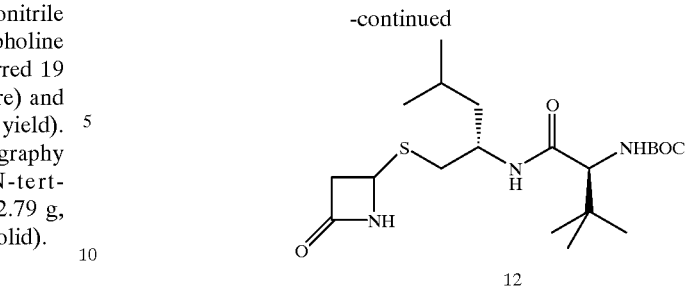

By following the same procedure as in example 1, step C but using the 11 from step B as starting material and 5 as reagent, compound 12 is obtained as a pale yellow oil.

$^1$H NMR (400 MHz, CDCl$_3$) δ 7.18 (d, 1H), 5.77 (d, 0.5H), 5.59 (d, 0.5H), 5.18–5.03 (m, 1H), 4.83 (dd, 0.5H), 4.70 (dd, 0.5H), 4.09–4.00 (m, 1H), 3.73 (d, 1H), 3.40 (dd, 0.5H), 3.34 (dd, 0.5H), 2.91–2.83 (m, 1H), 2.75 (dd, 0.5H), 2.68–2.61 (m, 1H), 2.56 (dd, 0.5H), 1.70–1.59 (m, 1H), 1.45 (s, 9H), 1.42–1.28 (m, 2H), 1.03 (s, 4.5H), 1.01 (s, 4.5H), 0.94–0.87 (d on d, 6H).

Step D The title compound of this example (13)

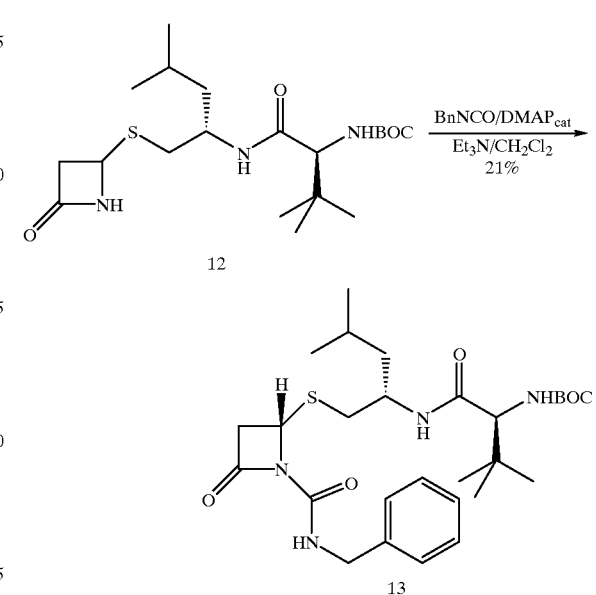

By following the same procedure as in example 1, step D but using 12 from step C as starting material and benzyl isocyanate as reagent, the title compound of this example 13 is obtained as white solid (the more polar diastereoisomer).

1H NMR (400 MHz, CDCl$_3$) δ 7.36–7.28 (m, 5H), 6.90 (br s, 1H), 6.29 (d, J 8.6 Hz, 1H), 5.23 (d, J=9.2 Hz, 1H), 5.18 (dd, J=2.9, 5.7 Hz, 1H), 4.53 (dd, J=6.2, 14.9 Hz, 1H), 4.44 (dd, J=6.2, 14.9 Hz, 1H), 4.35–4.25 (m, 1H), 3.81 (d, J=9.5 Hz, 1H), 3.50 (dd, J=5.7, 16.2 Hz, 1H), 3.17 (dd, J=5.1, 13.7 Hz, 1H), 3.15–3.05 (m, 1H), 2.91 (dd, J=2.9, 16.2 Hz, 1H), 1.63–1.35 (m, 3H), 1.54 (s, 9H), 1.41 (s, 9H), 0.99 (s, 9H), 0.91 (d, J=4.8 Hz, 3H), 0.89 (d, J=4.8 Hz, 3H); IR (KCl) ν 1774, 1703 cm$^{-1}$; FAB MS m/z 549 (MH$^+$) ; HRMS calcd for C$_{28}$H$_{45}$N$_4$O$_5$S$_1$: 549.3111 (MH$^+$); found: 543.3100.

Example 3

Preparation of 3(R)-methyl-4(S)-(pyridin-2-ylmethylthio)azetidin-2-one-1-carboxylic acid (1 (R)-phenylpropyl)amide hydrochloride (16).

(This compound was prepared solely for purposes of asserting the stereochemistry of compounds of examples 1 and 2. The establishment of the stereochemistry of the methylated lactam ring at position 3 and 4 ensured the assignment of the proper stereochemistry (S) by NMR studies at position 4 for compounds of examples 1 and 2.)

Step A 3(R)-methyl-4(S)-(pyridin-2-yl methylthio)azetidin-2-one hydrochloride (15)

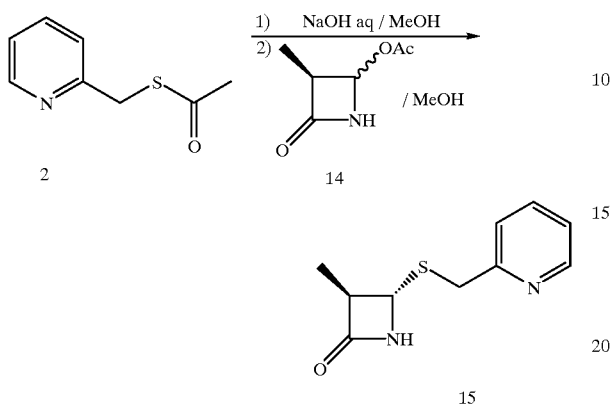

By following the same procedure as in example 1, step C but using 3(R)-methyl-4(S)-acetoxyazetidin-2-one (P. E. Finke et al., *J. Med. Chem.* 1995, 38, 2449) as starting material and the 2-picolyl thioacetate 2 from example 1 step A as reagent, compound 15 is obtained as a white solid.

$^1$H NMR (400 MHz, CDCl$_3$) δ8.53 (d, 1H), 7.68 (d, 1H), 7.33 (d, 1H), 7.21 (t, 1H), 6.60 (br s, 1H), 4.51 (d, 1H), 3.95 (s, 2H), 3.06 (q, 1H), 1.33 (d, 3H).

Step B 3(R)-methyl-4(S)-(pyridin-2-yl methylthio)azetidin-2-one-1-carboxylic acid (1(R)-phenylpropyl)amide hydrochloride (16)

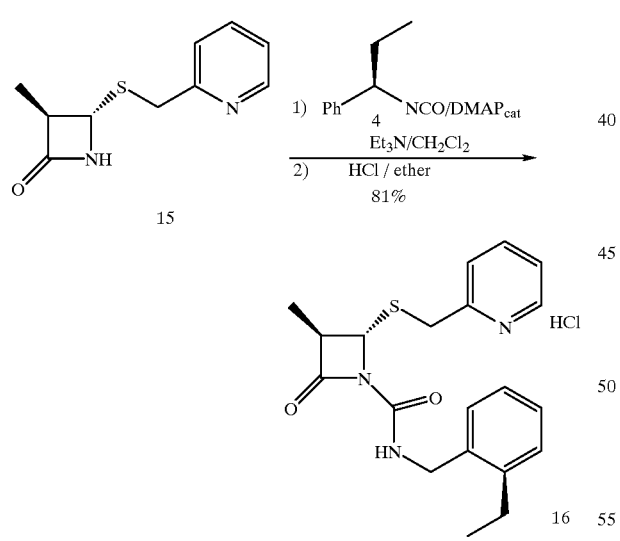

By following the same procedure as in example 1, step D but using the azetidinone from step A of this example as starting material and (1R)-phenylpropyl isocyanate 4 as reagent, compound 16 is obtained as a white solid after treatment with HCl in Et$_2$O.

$^1$H NMR (400MHz, DMSO-D6) δ8.63 (d, J=4.8 Hz, 1H), 8.06 (t, J=7.6 Hz, 1H), 7.67 (d, J=7.6 Hz, 1H), 7.54 (t, J=6.0 Hz, 1H), 7.36–7.31 (m, 4H), 7.27–7.23 (m, 1H), 7.19 (d, J=8.3 Hz, 1H), 5.02 (d, J=3.2 Hz, 1H), 4.66 (q, J=7.6 Hz, 1H), 4.42 (d, J=14.0 Hz, 1H), 4.26 (d, J=14.0 Hz, 1H), 3.29 (ddd, J=3.2, 7.2, 7.2 Hz, 1H), 1.87–1.73 (m, 2H), 1.21 (d, J=7.3 Hz, 3H), 0.83 (t, J=7.3 Hz, 3H); IR (KBr) v 3359, 1769, 1698 cm$^{-1}$; FAB MS m/z 370 (MH$^+$); HRMS calcd for C$_{20}$H$_{24}$N$_3$O$_2$S$_1$: 370.1589 (MH$^+$); found: 370.1602

Example 4

Preparation of 4-[N-t-butyloxycarbonyl-L-leucinoxy]-azetidin-2-one-1-carboxylic acid benzyl amide (19) (the 4R isomer is shown in Table 2, entry 201)

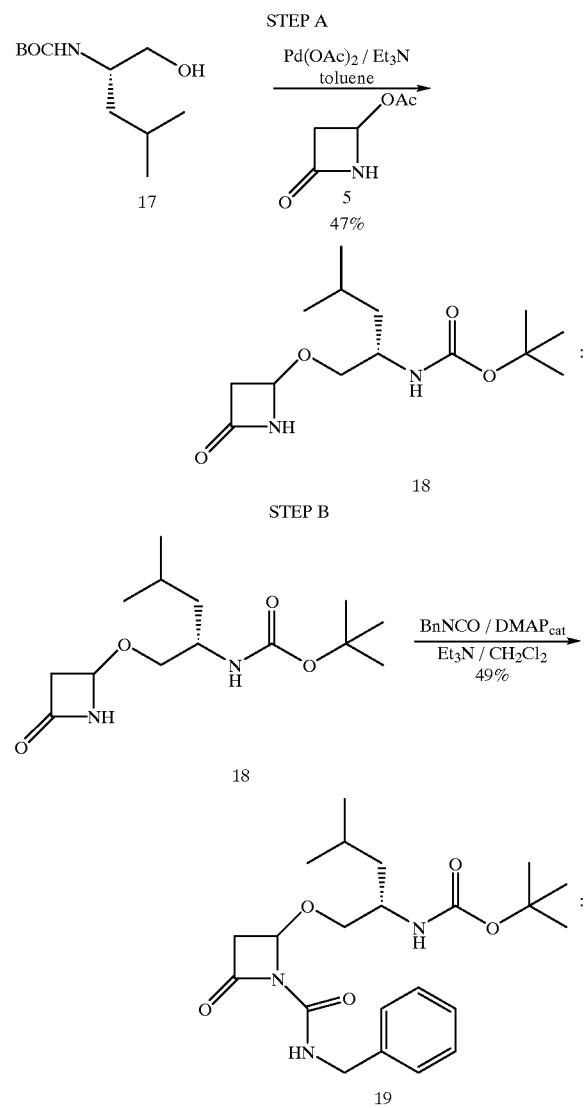

Step A 4-[N-t-butyloxycarbonyl-L-leucinoxy]-azetidin-2-one (18).

To a solution of L-BOC-leucinol 17 (1.0 g, 4.6 mmol) and Pd(OAc)$_2$ (155 mg, 0.69 mmnol) in toluene (15 mL) was added dropwise a solution of 4-acetoxyazetidinone 5 (654 mg, 5.06 mmol) and triethylamine (700 μL, 5.06 mmol) in toluene (8 mL). The resulting mixture was stirred 20 hr at room temperature and a fresh solution of 4-acetoxyazetidinone 5 (218 mg, 1.70 mmol) and triethylamine (230 μL, 1.70 mmol) in toluene (5 mL) was slowly added. After two days of stirring, the mixture was filtered on a pad of Celite, then poured in water (20 mL) and extracted with EtOAc (2×20 mL). The combined organic phases were washed with water (20 mL), dried with MgSO$_4$ and evaporated under vacuum. The residue was purified by flash chromatography (SiO$_2$, 30–40% EtOAc-hexane) affording 18 (622 mg, 47%) as a pale yellow oil.

$^1$H NMR (400 MHz, CDCl$_3$) δ6.75 (br s, 1H), 5.06 (ddd, J=1.3, 2.5, 10.0 Hz, 1H), 4.55 (d, J=8.0 Hz, 1H), 3.80 (br s, 1H), 3.53–3.43 (m, 2H), 3.13–3.07 (m, 1H), 2.86 (d, J=15.9 Hz, 1H), 1.70–1.60 (m, 1H), 1.45 (s, 9H), 1.41–1.24 (m, 2H), 0.93 (d, J=7.3 Hz, 6H).

Step B 4-[N-t-butyloxycarbonyl-L-leucinoxy]-azetidin-2-one-1-carboxylic acid benzyl amide (19).

By following the same procedure as in example 1, step D but using 18 from step A as starting material and benzyl-isocyanate as reagent is obtained 4-[N-t-butyloxycarbonyl-L-leucinoxy]-azetidin-2-one-1-carboxylic acid benzyl amide 19 as white solid (as 1:1 mixture of diastereoisomers).

$^1$H NMR (400 MHz, CDCl$_3$) δ 7.36–7.25 (m, 5H), 6.94–6.89 (m, 1H), 5.42–5.40 (m, 1H), 4.65–4.51 (m, 1H), 4.48–4.45 (m, 2H), 4.00–3.66 (m, 3H), 3.27–3.20 (m, 1H), 2.93 (dd, J=1.9, 16.2 Hz, 1H), 1.71–1.61 (m, 1H), 1.44 (s, 9H), 1.37–1.23 (m, 2H), 0.92 (d, J=6.4 Hz, 6H); IR (NaCl) v 3356, 2957, 1773, 1699, 1653 cm$^{-1}$; FAB MS m/z 420 (MH$^+$); HRMS calcd for C$_{28}$H$_{45}$N$_4$O$_6$: 533.3339 (MH$^+$); found: 533.3347.

Example 5

Preparation of 4-[N-t-butyloxycarbonyl-L-t-butylglycine-L-leucinoxy]-azetidin-2-one-1-carboxylic acid benzyl amide (22) (the 4R isomer is shown in Table 2, entry 202)

Step A 4-[N-t-butyloxycarbonyl-L-t-butylglycine-L-leucinoxy]-azetidin-2-one (21).

To a solution of the alcohol from example 2 step A 20 (1.02 g, 3.09 mmol) and Pd(OAc)$_2$ (139 mg, 0.62 mmol) in toluene (10 mL) was added dropwise a solution of 4-acetoxyazetidinone 5 (439 mg, 3.40 mmol) and triethylamine (475 μL, 3.40 mmol) in toluene (5 mL). The resulting mixture was stirred 20 hr at room temperature and a fresh solution of 4-acetoxyazetidinone 5 (218 mg, 1.70 mmol) and triethylamine (230 μL, 1.70 mmol) in toluene (2 mL) was slowly added. After two days of stirring, the mixture was filtered on a pad of Celite, then poured in water (20 mL) and extracted with EtOAc (2×20 mL). The combined organic phases were washed with water (20 mL), dried with MgSO$_4$ and evaporated under vacuum. The residue was purified by flash chromatography (SiO$_2$, 55% EtOAc-hexane) affording 21 (565 mg, 46%) as a pale yellow oil (mixture of diastereoisomers at C4).

$^1$H NMR (400 MHz, CDCl$_3$) δ6.95 (s, 0.5H), 6.88 (s, 0.5H), 5.91 (d, J=7.9 Hz, 1H), 5.30–5.15 (m, 1H), 5.05 (ddd, J=1.2, 5.1, 10.5 Hz, 1H), 4.25–4.13 (m, 1H), 3.75–3.04 (n, 1H), 2.85 (d, J=15.0 Hz, 1H), 1.66–1.55 (m, 1H), 1.43 (s, 9H), 1.41–1.26 (m, 2H), 0.99 (s, 9H), 0.91 (d, J=6.4 Hz, 3H), 0.90 (d, J=6.4 Hz, 3H).

Step B 4-[N-t-butyloxycarbonyl-L-t-butylglycine-L-leucinoxy]-azetidin-2-one-1-carboxylic acid benzylamide (22).

By following the same procedure as in example 1, step D but using 21 from step A as starting material and benzyl-isocyanate as reagent is obtained 4-[N-t-butyloxycarbonyl-L-t-butylgycine-L-leucinoxy]-azetidin-2-one-1-carboxylic acid benzyl amide 22 as white solid (as 1:1 mixture of diastereoisomers).

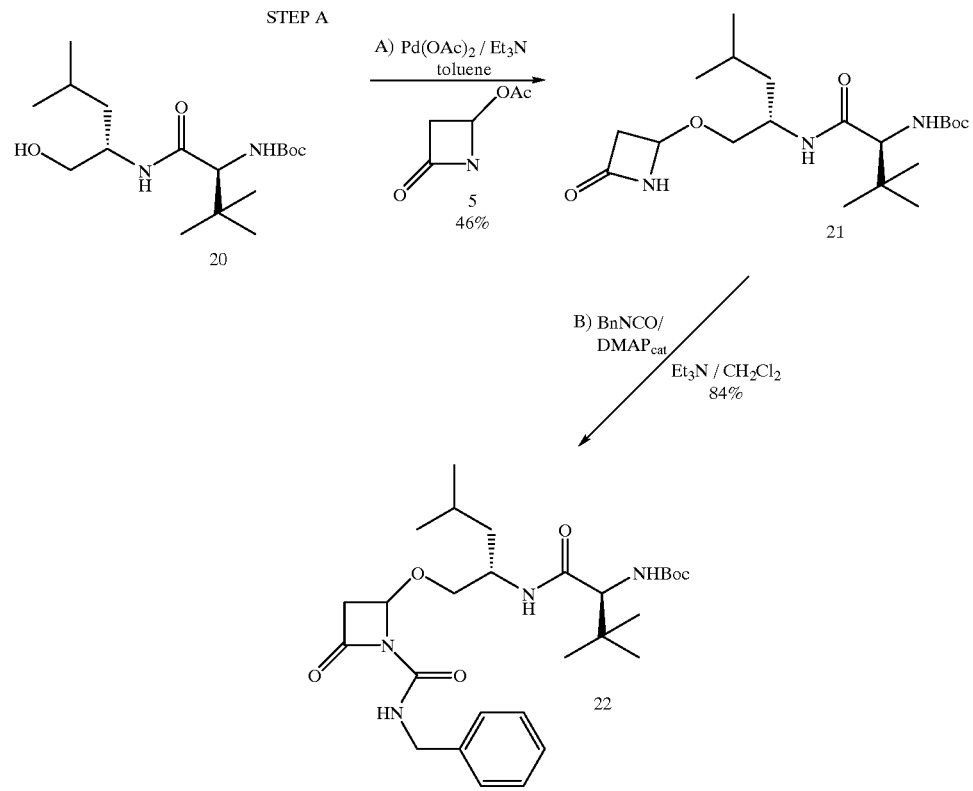

$^1$H NMR (400 MHz, CDCl$_3$) δ 7.36–7.26 (m, 5H), 6.94–6.89 (m, 1H), 6.03 (d, J=8.6 Hz, 0.4H), 5.64 (d, J=8.6

Hz, 0.6H), 5.43–5.37 (m, 1H), 5.30–5.24 (m, 1H), 4.50–4.46 (m, 1H), 4.30–4.17 (m, 1H), 4.06–3.97 (m, 1H), 3.88–3.69 (m, 2H), 3.25 (ddd, J=1.3, 4.5, 16.2 Hz, 1H), 2.93 (ddd, J=1.9, 6.4, 16.2 Hz, 1H), 1.65–1.57 (m, 1H), 1.43 (s, 5.4H), 1.42 (s, 3.6H), 1.41–1.26 (m, 2H), 0.98 (s,9H); 0.91 (d, J=6.4 Hz, 6H); IR (NaCl) v 3356, 2957, 1773, 1699, 1653 cm$^{-1}$; FAB MS m/z 420 (MH$^+$); HRMS calcd for $C_{28}H_{45}N_4O_6$: 533.3339 (MH$^+$); found: 533.3347.

Example 6

Anti-herpes Activity

The following two assays (A and B) were used to evaluate anti HCMV activity.

1. HCMV $N_o$ Protease Assay

Material & Methods: Fluorescence measurements were recorded on a Perkin-Elmer LS-50B spectrofluorimeter equipped with a plate reader accessory. UV measurements were recorded on a Thermomax® microplate reader from Molecular Devices Corporation, Menlo Park, Calif., USA.

HCMV $N_o$ protease was assayed with an internally quenched fluorogenic substrate based on the maturation cleavage site (Abz-VVNASSRLY(3-NO$_2$)R—OH, $K_{cat}/K_M$=260 M$^{-1}$s$^{-1}$). The fluorescence increase upon cleavage of the Ala-Ser amide bond was monitored using excitation λ=312 nm (slit 2.5 nm) and emission λ=415 nm (slit nm). A protocol adaptable to a 96-well plate format was designed for the determination of IC$_{50}$ values of inhibitors.

Briefly, HCMV $N_o$ was incubated for 2.5 h at 30° with a range of sequentially diluted inhibitors concentrations (300 to 0.06 1 μM depending on the potency of each compound). After this period, enzymatic hydrolysis of the fluorogenic substrate in the absence of inhibitor led to about a 30% conversion. No quenching was required before fluorescence measurement since the total scanning time by the plate reader accessory was brief relative to the duration of the reaction. The aqueous incubation buffer contained 50 mM tris(hydroxymethyl)aminomethane-HCl pH 8, 0.5M Na$_2$SO$_4$, 50 mM NaCl, 0.1 mM EDTA, 1 mM tris(2-carboxyethyl)phosphine.HCl, 3% v/v DMSO and 0.05% w/v casein. The final concentrations of HCMV $N_o$ protease (expressed in terms of total monomer concentration) and substrate were 100 nM and 5 μM respectively. IC$_{50}$ values were obtained through fitting of the inhibition curve to a competitive inhibition model using SAS NLIN procedure. The mode of inhibition was determined by measurements of the initial rates (in cuvettes) at various substrate concentrations in the buffer as described above. The IC$_{50}$ values listed in the following tables were obtained according to this assay.

B. Plaque Reduction Assay (PRA): Hs-68 cells (ATCC # CRL 1635) were seeded in 12-well plates at 83,000 cells/well in 1 mL of DMEM medium (Gibco Canada Inc.) supplemented with 10% fetal bovine serum (FBS, Gibco Canada Inc.). The plates were incubated for 3 days at 37° to allow the cells to reach 80–90% confluency prior to the assay.

The medium was removed from the cells by aspiration. The cells were then infected with approximately 50 PFU of HCMV (strain AD169, ATCC VR-538) in DMEM medium supplemented with 5% inactivated FBS (assay medium). (DMEM medium is commercially available and has been described by R. Dulbecco et al., Virology 1959, 8, 396.) The virus was allowed to adsorb to cells for 2 h at 37°. Following viral adsorption, the medium was removed from the wells by aspiration. The cells were then incubated with or without 1 mL of appropriate concentrations of test reagent in assay medium. Occasionally, test compounds were added 24 h post-infection. After 4 days of incubation at 37°, the medium was exchanged with fresh medium containing test compound and 4 days later the cells were fixed with 1% aqueous formaldehyde and stained with a 2% violet solution in 20% ethanol in water. Microscopic plaques were counted using a stereomicroscope. Drug effects were calculated as a percent reduction in the number of plaques in the presence of each drug concentration compared to the number observed in the absence of drug. Ganciclovir was used as a positive control in all experiments.

The EC$_{50}$ values obtained according to this assay for certain azetidine derivatives of this invention are listed in the following table under the heading EC$_{50}$.

Example 7

In conjunction with the appropriate starting materials and intermediates, the procedures of examples 1 and 2 can be used to prepare other compounds of formula 1. Examples of compounds thus prepared are listed in the following Table 1 together with mass spectrum data for the compounds, and results from the assays A and B of example 6.

Cytotoxic effects noted as TC$_{50}$ in the following tables were determined according to the tetrazolium salt (MTT) metabolic assay, F. Denizot and F. Lang, J. Immun. Meth., 1986, 89, 271.

Symbols used in the following table includes Ph: phenyl; Bn: benzyl; Boc: tert-butyloxycarbonyl; Me: methyl and Tbg: tert-butylglycine.

TABLE 1

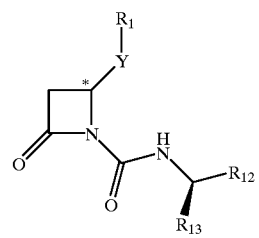

| Entry No. | R$_1$ | Y | R$_{12}$ | R$_{13}$ | *(R) or (S) | IC$_{50}$ (μM) | EC$_{50}$ (μM) | TC$_{50}$ (μM) | MS FAB |
|---|---|---|---|---|---|---|---|---|---|
| 101 | CH$_2$—(S)CH(CH$_2$CHMe$_2$)—NH—Tbg—Boc | S | Ph | H | S | 0.40 | >11 | >11 | 549 |
| 102 | Ph | S | Ph | Me | S | 1.9 | 40 | >100 | 327 |
| 103 | CH$_2$Ph | S | Ph | Me | S | 12.4 | >5 | >5 | 341 |

TABLE 1-continued

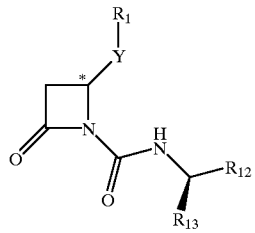

| Entry No. | $R_1$ | Y | $R_{12}$ | $R_{13}$ | *(R) or (S) | $IC_{50}$ (μM) | $EC_{50}$ (μM) | $TC_{50}$ (μM) | MS FAB |
|---|---|---|---|---|---|---|---|---|---|
| 104 | $CH_2CH_2Ph$ | S | Ph | Me | S | 6.5 | >4 | >4 | 355 |
| 105 | $CH_2$—(S)CH($CH_2CH_2SO_2Me$)—NH—Tbg—Boc | S | Ph | Me | S | 0.2 | 110 | >250 | 613 |
| 106 | $CH_2$—(S)CH($CH_2CH_2SO_2Me$)—NH—Tbg—Boc | S | Ph | Me | R | 0.62 | 230 | >250 | 613 |
| 107 | Ph | SO | Ph | Me | R | 9 | | | 343 |
| 108 | Ph | SO | Ph | Me | S | 4 | | | 343 |
| 109 | 4-pyridinylmethyl | S | Ph | Me | S | 2.1 | 65 | >250 | 342 |
| 110 | 3-pyridinylmethyl | S | Ph | Me | S | 2.0 | 96 | >200 | 342 |
| 111 | 2-pyridinylmethyl | S | Ph | Me | S | 2.5 | 60 | 180 | 342 |
| 112 | $CH_2COPh$ | S | Ph | Me | S | 1.0 | >37 | >37 | 369 |
| 113 | 2-pyridinylmethyl | S | $CH_2CH_2OBn$ | H | S | 6.3 | 140 | 100 | 372 |
| 114 | 2-pyridinylmethyl | S | Ph | Et | S | 1.2 | 80 | >200 | 356 |
| 115 | $CH_2$—(S)CH($CH_2CHMe_2$)—NH—Tbg—$COCH_2CMe_3$ | S | Ph | Et | S | <0.06 | >250 | >250 | 576 |
| 116 | 2-pyridinylmethyl | S | Ph | $CH_2OH$ | S | 3.6 | | | 358 |

ND: Not Determined
*: Configuration at position 4 of the lactam ring

TABLE 2

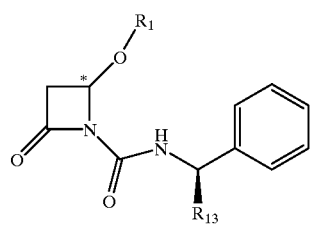

| Entry No. | $R_1$ | * (R) or (S) | $R_{13}$ | $IC_{50}$ (μM) | $EC_{50}$ (μM) | $TC_{50}$ (μM) | MS FAB |
|---|---|---|---|---|---|---|---|
| 201 | $CH_2$—CH($CH_2CHMe_2$)NH—Boc | R | H | 44 | | | 420 |
| 202 | $CH_2$—CH($CH_2CHMe_2$)NH—Tbg—Boc | R | H | 1.3 | 64 | >52 | 533 |
| 203 | $CH_2$—CH($CH_2CHMe_2$)NH—Tbg—Boc | S | Me | 0.32 | >49 | >49 | 547 |
| 204 | $CH_2$—CH($CH_2CHMe_2$)NH—Tbg—$COCH_2$-t-Bu | R | H | 0.16 | | | 531 |
| 205 | $CH_2CH[CH_2C(O)N\{(CH_3)(C(CH_3)_3)\}]$—NH—$COCH_2$-t-Bu | R | H | 5 | >250 | >250 | 489 |
| 206 | Ph-4-Cl | R | Me | 1.6 | | | 345 |
| 207 | Ph-4-Cl | S | Me | 0.8 | 250 | >250 | 345 |
| 208 | $CH_2CH_2NHC(O)$—Ph-4-$COCH_2$-t-Bu | S | Me | 21 | | | 495 |
| 209 | (R)$CHMeCO_2Me$ | R | Me | 21.5 | | | 321 |
| 210 | (S)$CHMeCO_2Me$ | S | Me | 3.8 | | | 321 |

What is claimed is:

1. A compound of formula 1 selected from the group consisting of:

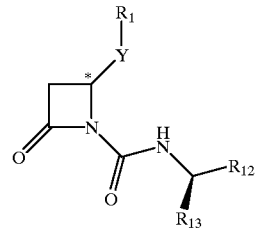
(1)

wherein $R_1$, Y, $R_{12}$ and $R_{13}$ are as defined below:

| Entry No. | $R_1$ | Y |
|---|---|---|
| 101 | CH$_2$—(S)CH(CH$_2$CHMe$_2$)—NH-Tbg-Boc | S |
| 102 | Ph | S |
| 103 | CH$_2$Ph | S |
| 104 | CH$_2$CH$_2$Ph | S |
| 105 | CH$_2$—(S)CH(CH$_2$CH$_2$SO$_2$Me)—NH-Tbg-Boc | S |
| 106 | CH$_2$—(S)CH(CH$_2$CH$_2$SO$_2$Me)—NH-Tbg-Boc | S |
| 107 | Ph | SO |
| 108 | Ph | SO |
| 109 | 4-pyridinylmethyl | S |
| 110 | 3-pyridinylmethyl | S |
| 111 | 2-pyridinylmethyl | S |
| 112 | CH$_2$COPh | S |
| 113 | 2-pyridinylmethyl | S |
| 114 | 2-pyridinylmethyl | S |
| 115 | CH$_2$—(S)CH(CH$_2$CHMe$_2$)—NH-Tbg-COCH$_2$CMe$_3$ | S |
| 116 | 2-pyridinylmethyl | S |

| Entry No. | $R_{12}$ | $R_{13}$ | *(R) or (S) |
|---|---|---|---|
| 101 | Ph | H | S |
| 102 | Ph | Me | S |
| 103 | Ph | Me | S |
| 104 | Ph | Me | S |
| 105 | Ph | Me | S |
| 106 | Ph | Me | R |
| 107 | Ph | Me | R |
| 108 | Ph | Me | S |
| 109 | Ph | Me | S |
| 110 | Ph | Me | S |
| 111 | Ph | Me | S |
| 112 | Ph | Me | S |
| 113 | CH$_2$CH$_2$OBn | H | S |
| 114 | Ph | Et | S |
| 115 | Ph | Et | S |
| 116 | Ph | CH$_2$OH | S | or a therapeutically acceptable acid addition salt thereof, wherein Tbg is tert-butylglycine, Me is methyl, Et is ethyl, Bn is benzyl, Ph is phenyl and Boc is tert-butyloxycarbonyl.

2. A compound of formula 2 selected from the group consisting of:

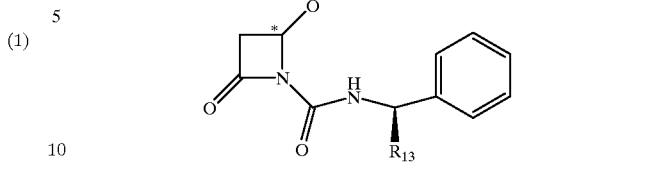
(2)

wherein $R_1$, and $R_{13}$ are as defined below:

| Entry No. | $R_1$ | *(R) or (S) | $R_{13}$ |
|---|---|---|---|
| 201 | CH$_2$—CH(CH$_2$CHMe$_2$)NH-Boc | R | H |
| 202 | CH$_2$—CH(CH$_2$CHMe$_2$)NH-Tbg-Boc | R | H |
| 203 | CH$_2$—CH(CH$_2$CHMe$_2$)NH-Tbg-Boc | S | Me |
| 204 | CH$_2$—CH(CH$_2$CHMe$_2$)NH-Tbg-COCH$_2$-t-Bu | R | H |
| 205 | CH$_2$CH[CH$_2$C(O)N{(CH$_3$)(C(CH$_3$)$_3$)}]-NH—COCH$_2$-t-Bu | R | H |
| 206 | Ph-4-Cl | R | Me |
| 207 | Ph-4-Cl | S | Me |
| 208 | CH$_2$CH$_2$NHC(O)-Ph-4-COCH$_2$-t-Bu | S | Me |
| 209 | (R)CHMeCO$_2$Me | R | Me |
| 210 | (S)CHMeCO$_2$Me | S | Me | or a therepeotically acceptable acid addition salt thereof, wherein Tbg is tert-butylglycine, Me is methyl, Ph is phenyl, t-Bu is tert- butyl and Boc is tert-butyloxycarbonyl.

3. The compound of formula 2 according to claim 2, in combination with another conventional anti-herpes compound, selected from the group consisting of: ganciclovir, foscamet, acyclovir, valacyclovir, famciclovir, cidofovir, penciclovir and lobucavir.

4. The compound of formula 2 according to claim 2 in combination with an anti-retroviral compound, selected from the group consisting of: reverse transcriptase inhibitors and protease inhibitors.

5. A pharmaceutical composition for treating cytomegalovirus infections in a mammal, including human, comprising the compound of formula 1 according to claim 1, or a therapeutically acceptable salt thereof, in admixture with a pharmaceutically acceptable carrier.

6. A method for treating cytomegalovirus infections in a mammal, including human, comprising administering thereto an effective amount of the compound of formula 1 according to claim 1, or a therapeutically acceptable salt thereof.

7. A method for protecting infected human cells against cytomegalovirus pathogenesis comprising treating said infected cells with an anti-cytomegalovirus effective amount of the compound of formula 1 according to claim 1, or a therapeutically acceptable salt thereof.

8. The compound of formula 1 according to claim 1, in combination with another conventional anti-herpes compound, selected from the group consisting of:
ganciclovir, foscarnet, acyclovir, valacyclovir, famciclovir, cidofovir, penciclovir, and lobucavir.

9. The compound of formula 1 according to claim 1 in combination with an anti-retroviral compound, selected from the group consisting of: reverse transcriptase inhibitors and protease inhibitors.

10. A method of protecting infected human cells against cytomegavirlis pathogenesis comprising treating said infected cells with an anti-cytomegalovirus effective amount of the compound of formula 2 according to claim 2, or a therapeutically acceptable salt thereof.

11. The compound of formula 1 according to claim 1 selected from the group consisting of entries#: 101, 102, 103, 105, 106, 108, 109, 110, 111, 112, 14,115 and 116.

12. The compound of formula 1 according to claim 11 selected from the group consisting of entries #: 101, 102, 103, 105, 106, 112 and 115.

13. A method for treating cytomegalovirus infections in a manimal including human, comprising administering thereto an effective amount of the compound of formula 2 according to claim 2 or a therapeutically acceptable salt thereof.

14. The compound of formula 2 according to claim 2 selected from the group consisting of entries #: 202, 203, 204, 205, 206, 207 and 210.

15. The compound of formula 2 according to claim 14 selected from the group consisting of entries #: 202, 203, 204 and 207.

16. A pharmaceutical composition for treating cytomegalovirus infections in a mammal, including an comprising the compound of formula 2 according to claim 2, or therapeutically acceptable salt thereof, in admixture with a pharmaceutically acceptable carrier.

* * * * *